United States Patent [19]

Mitchell

[11] 4,412,983
[45] Nov. 1, 1983

[54] DENTIFRICES CONTAINING AMORPHOUS SILICA

[75] Inventor: Robert L. Mitchell, Somerset, N.J.

[73] Assignee: Colgate-Palmolive Company, New York, N.Y.

[21] Appl. No.: 423,951

[22] Filed: Sep. 27, 1982

Related U.S. Application Data

[60] Continuation of Ser. No. 58,600, Jul. 18, 1979, abandoned, which is a continuation-in-part of Ser. No. 966,451, Dec. 4, 1978, abandoned, which is a division of Ser. No. 770,344, Feb. 22, 1977, Pat. No. 4,141,969.

[51] Int. Cl.³ .............................. A61K 7/18
[52] U.S. Cl. ........................... 424/52; 206/524.4
[58] Field of Search ................. 424/52; 206/524.4

[56] References Cited

U.S. PATENT DOCUMENTS 4,141,969  2/1979  Mitchell ............................. 424/52
4,159,280  6/1979  Wason ............................ 206/524.4

Primary Examiner—Shep K. Rose
Attorney, Agent, or Firm—Robert L. Stone; Herbert S. Sylvester; Murray M. Grill

[57] ABSTRACT

Dentifrice containing a compound which provides fluorine, amorphous silica polishing agent and an additive which supplies calcium ions. The dentifrice is compatible with an unlined aluminum container.

12 Claims, No Drawings

DENTIFRICES CONTAINING AMORPHOUS SILICA

This is a continuation of application Ser. No. 58,600 filed July 18, 1979, now abandoned which is a continuation-in-part application of Ser. No. 966,451, filed Dec. 4, 1978, now abandoned, which is a division of application Ser. No. 770,344, filed Feb. 22, 1977, now U.S. Pat. No. 4,191,969 issued Feb. 27, 1979.

This invention relates to a dentifrice containing an amorphous silica polishing agent. Amorphous silica polishing agents for dentifrices which are synthetic, precipitated materials and include amounts of combined alumina have been described in U.S. Pat. Nos. 3,911,102, 3,911,104 and 3,906,090, as well as in aspects of U.S. Pat. Nos. 3,893,840 and 3,928,541. Further amorphous precipitated silica polishing agents have been developed which are substantially free of alumina, except for that which may be present as an impurity. Such polishing agents have been described in further aspects of U.S. Pat. Nos. 3,893,840 and 3,928,541 as well as in U.S. Pat. No. 3,960,586.

These agents which are substantially free of alumina have been found to have desirable polishing properties. However, when employed in toothpastes which include a compound which provides fluorine such as sodium fluoride or sodium monofluorophosphate they generally are incompatible with the unlined surface of an aluminum dentifrice container, in particular causing the swelling and formation of gas on the tube wall and also corroding the wall itself. Occasional lots of the amorphous silica are compatible with the aluminum surface. However, it is difficult to reproduce such lots.

It is an advantage of this invention that an additive is provided which renders amorphous silica polishing agent in the presence of a compound which provides fluorine compatible with the surface of an unlined aluminum container. Other advantages will be apparent from consideration of the following disclosure.

In accordance with certain of its aspects this invention relates to a dental cream composition in an unlined aluminum container which is compatible with the surface of said unlined aluminum container, which composition comprises a dental vehicle and dispersed therein synthetic precipitated silica essentially free of alumina which silica has an aggregate particle size of about 2 to 20 microns and an essentially amorphous X-ray structure, a compound which provides fluorine in amount about 0.01-1% by weight and a calcium salt in amount to provide a stabilizing amount up to about 0.3% by weight of calcium ions in water to stabilize said dental cream in said unlined aluminum container.

In accordance with preferred aspects of the invention, the stability of the dental cream is enhanced by the presence of hydrated alumina, preferably alpha-alumina trihydrate in minor amount, such as about 0.25-10% by weight.

In accordance with further aspects of this invention, the dental cream is packaged in an unlined aluminum container or dental cream tube, with which it remains compatible upon aging.

The precipitated amorphous silica dental polishing agent is present in amount of about 5-50% by weight, preferably about 10-25%. The silica is essentially free of alumina (beyond that inherently present as impurity) and is typified by the description of such materials in U.S. Pat. Nos. 3,893,840, 3,928,541 and 3,960,586, the disclosures of which are incorporated herein by reference. Thus it can have a wet cake moisture content of less than about 75%, such as between about 50 and 70% (a low wet cake content); an oil absorption of less than about 125 cc/100 gm., e.g., less than about 110 cc/100 gm; a pack density of more than about 12 pounds/cubic foot; and a valley abrasion of more than about 5.0 mg. wire loss, e.g., about 10 mg to 168 mg. The surface area is typically less than about 120 $m^2/gm$, preferably about 30 $m^2/gm.$-100 $m^2/gm$.

The compound which contains and provides fluorine has a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride, ($SnF_2KF$), sodium hexafluorostannate, stannous chlorofluoride, sodium fluorzirconate and sodium monofluorophosphate. These materials, which dissociate or release fluorine containing ions in water are present in an effective but non-toxic amount providing about 0.01-1% by weight of fluorine. Sodium fluoride (about 0.02-2%) and sodium monofluorophosphate (about −0.075-7.6%) are preferred.

The calcium salt additive which stabilizes the dental cream of the invention in an unlined aluminum container may be a water-soluble or a substantially water-insoluble compound. The compound should be ionizable in water to provide an effective stabilizing amount to about 0.3% of calcium ions, such as at least about 0.0001% preferably at least about 0.00015%. Typical water soluble calcium salts include the chloride, bromide, iodide, acetate and nitrate. Substantially water-insoluble salts, such as the carbonate (solubility in water about 0.001%), metasilicate (solubility in water about 0.01%), and phosphate (solubility in water for dicalcium phosphate about 0.02%) may be used. It is noted that the phosphate moiety of dicalcium phosphate may exert a stabilizing effect independent of the calcium ions, even when less than about 0.01% of calcium ions would ionize.

Very small amounts of calcium from the water-insoluble calcium salt can be effective for stabilizing the dental cream in an unlined aluminum container. Thus, dental cream with as little as about 1% of the insoluble calcium salt in the dental cream is stable in an unlined aluminum tube. The insoluble salt may typically be employed in amount of about 1-5%, for instance about 1-3% for calcium carbonate and calcium metasilicate and about 2-5% for dicalcium phosphate (anhydrous, dihydrate or mixture thereof).

If desired the dental cream may contain a metallic salt additive to provide metal ions in addition to the calcium ions. Magnesium salts and particularly water-soluble magnesium salts such as magnesium chloride can be particularly desirable. Typical amounts of such additional metal ion are at least about 0.01% by weight, preferably about 0.01-0.3%.

A minor amount, e.g., at least about 0.25% of a hydrated alumina, such as alpha-alumina trihydrate, may be added to the dental cream. The hydrated alumina assists in polishing and reduces the tendency of the dental cream to separate into phases. The hydrated alumina can comprise about 10% by weight of the dental cream. About 1-2% by weight is preferred. The polishing ability of the dental cream may also be supplemented with a minor amount, e.g., about 0.5-5% by weight, preferably about 0.5-1%, of a hard abrasive, such as calcined alumina or zirconium silicate.

In the dental cream formulation, the liquids and solids are necessarily proportioned to form a creamy mass of desired consistency which is extrudible from a collapsible unlined aluminum container. In general, the liquids in the dental cream will comprise chiefly water, glycerine, aqueous solutions of sorbitol, propylene glycol, polyethylene glycol 400, etc., including suitable mixtures thereof. It is advantageous usually to use a mixture of both water and a humectant or binder such as glycerine or sorbitol. The total liquid content will generally be about 20-75% by weight of the formulation. It is preferred to use also a gelling agent in dental creams such as the natural and synthetic gums and gumlike materials, e.g., Irish moss, gum tragacanth, methyl cellulose, hydroxyethyl cellulose, sodium carboxymethyl cellulose, polyvinylpyrrolidone, and starch, usually in an amount up to about 10%, and preferably about 0.2-5% of the formulation. The preferred gelling agents are sodium carboxymethyl cellulose, methyl cellulose and hydroxyethyl cellulose.

Organic surface-active agents used in the compositions of the present invention to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monoglyceride monosulfates, such as sodium lauryl sulfate, alkyl aryl sulfonates, such as sodium dodecyl benezene sulfonate, higher alkyl sulfoacetates, higher fatty acid ester of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium and ethanol-amine salts of N-lauroyl, N-myristoyl or N-palmitoyl sarcosine which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of sorbitan monostearate with approximately 60 moles of ethylene oxide, condensates of ethylene oxide with propylene oxide condensates of propylene glycol (available under the trademark ("Pluronics") and amphoteric agents such as quaternized imidazole derivatives which are available under the trademark "Miranol" such as Miranol C₂M. Cationic surface-active germicides and antibacterial compounds such as di-isobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethanoxy groups mer molecule) and salts thereof with acids and compounds of the structure

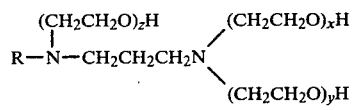

where R is a fatty alkyl group containing from about 12 to 18 carbon atoms, and x, y, and z total 3 or higher, as well as salts thereof with mineral or organic acids, may also be used. It is preferred to use from about 0.05 to 5% by weight of the foregoing surface-active materials in the instant oral preparations.

Various other materials may be incorporated in the oral preparations of this invention. Examples thereof are coloring or whitening agents, preservatives, silicone, chlorophyll compounds, ammoniated materials such as urea, diammoniumphosphate and mixtures thereof, and other constituents. These adjuvants are incorporated in the instant compositions in amounts which do not substantially adversely effect the properties and characteristics desired and are selected and used in proper amount depending upon the particular type of preparation involved.

The dental cream typically has a pH (determined directly on the cream) of about 4.5 to 10, preferably about 5-9. If desired, the pH may be adjusted with an acidic material, such as benzoic or citric acid, or an alkaline material, such as sodium hydroxide to achieve a particular value. Buffering agents, e.g., phosphate buffers, may be used.

The dental cream may be prepared by conventional means with the calcium (and if present, other metal salt) being added to the cream gel vehicle. The gel is formed by dispersing a gelling agent with a preservative (e.g., sodium benzoate) and humectant. Water may be present too. Polishing material, surface-active agent, the additive providing calcium ion and flavor are then added.

The following specific examples are further illustrative of the nature of the present invention but it is understood that the invention is not limited thereto. The compositions are prepared in the usual manner and all amounts and proportions in this specification are by weight unless otherwise specified.

EXAMPLE 1

The following dental creams are prepared and placed in an unlined aluminum toothpaste tube and aged at 43° C. and 49° C.

| INGREDIENTS | PARTS | | |
|---|---|---|---|
| | A | B | C |
| Glycerine | 25 | 25 | 25 |
| Sodium benzoate | 0.5 | 0.5 | 0.5 |
| Sodium saccharin | 0.2 | 0.2 | 0.2 |
| Sodium carboxymethyl cellulose | 1.1 | 1.0 | 1.0 |
| Sodium monofluorophosphate | 0.76 | 0.76 | 0.76 |
| Amorphous silica | 30 | 28 | 30 |
| Anhydrous dicalcium phosphate | — | 5 | — |
| Calcium carbonate | — | — | 1 |
| Calcined alumina | 0.5 | — | 0.5 |
| Alpha alumina trihydrate | 1 | — | 1 |
| Titanium dioxide | 0.5 | 0.5 | — |
| Sodium lauryl sulfate | 1.5 | 1.5 | 1.5 |

-continued

| INGREDIENTS | PARTS | | |
|---|---|---|---|
| | A | B | C |
| Flavor | 1 | 1 | 1 |
| Water | Q.S. to 100 | Q.S. to 100 | Q.S. to 100 |

The amorphous silica is a synthetic product substantially free of alumina (Al content being only 0.20%) in accordance with U.S. Pat. No. 3,893,840; for instance having an oil absorption of 108 cc/100 gm and a surface area of 64 m²/gm. Its Si content is 38.2%. Its trace element content is:

| | % |
|---|---|
| Ca | 0.0025 |
| Fe | 0.35 |
| Na | 1.70 |
| Al | 0.20 |
| Mg | 0.008 |

Upon aging for 9 weeks at 43° C. and 49° C., dental cream A undergoes tube swelling and black stain on its tube with wet tube walls. Further there is evidence of air on the tube wall. It is not compatible with the unlined aluminum toothpaste tube. On the other hand dental creams B and C are substantially compatible with their tubes undergoing at most no more than traces of air on the tube walls and slight staining.

EXAMPLE 2

The following dental creams are tubed in unlined aluminum toothpaste tubes. After aging for 3, 6 and 9 weeks at 43° C. and 49° C. they are observed to be substantially compatible with the tubes.

| INGREDIENTS | PARTS BY WEIGHT DENTAL CREAM | |
|---|---|---|
| | A | B |
| Glycerine | 25 | 25 |
| Sodium benzoate | 0.5 | 0.5 |
| Sodium saccharin | 0.2 | 0.2 |
| Sodium carboxymethyl cellulose | 1 | 1 |
| Sodium monofluorophosphate | 0.76 | 0.76 |
| Amorphous silica (as in Example 1) | 28 | 28 |
| Calcined alumina | 0.5 | 0.5 |
| Alpha alumina trihydrate | — | 1 |
| Calcium metasilicate | 2 | 2 |
| Titanium dioxide | 0.5 | 0.5 |
| Sodium lauryl sulfate | 1.5 | 1.5 |
| Flavor | 1 | 1 |
| Water | Q.S. to 100 | Q.S. to 100 |

It is understood that a small amount of alumina is generally present as impurity in the synthetic precipitated silica. Such silicas which are "essentially free of alumina" typically contain no more than about 0.4% by weight aluminum, e.g. about 0.04%–0.2% by weight aluminum.

Although this invention has been described with reference to specific examples, it will be apparent to one skilled in the art that various modifications may be made thereto which fall within its scope.

I claim:

1. A dental cream composition compatible with the surface of an unlined aluminum container and contained in said container, comprising dental vehicle and dispersed therein synthetic precipitated silica essentially free of alumina which silica has an aggregrate particle size of about 2 to 20 microns and an essentially amorphous X-ray structure, a compound which provides fluorine in amount of about 0.01% to 1% by weight and a calcium salt selected from the group consisting of calcium carbonate, calcium metasilicate and calcium phosphate in amount to provide at least about 0.01% to about 0.3% by weight of calcium in water.

2. The dental cream composition claimed in claim 1 wherein said synthetic precipitated amorphous silica is present in amount of about 5 to 50% by weight.

3. The dental cream composition claimed in claim 2 wherein said synthetic precipitated amorphous silica is present in amount of about 10 to 35%.

4. The dental cream composition claimed in claim 2 wherein said synthetic precipitated amorphous silica has a wet cake moisture content of less than about 75%, and oil absorption of less than about 125 cc/100 gm, a pack density of more than about 12 pounds/cubic foot, a valley abrasion of more than about 5.0 mg wire loss and a surface area of less than about 120 m²/gm.

5. The dental cream composition claimed in claim 1 wherein said compound which provides fluorine is selected from the group consisting of sodium fluoride and sodium monofluorophosphate.

6. The dental cream composition claimed in claim 5 wherein said compound which provides fluorine is sodium monofluorophosphate.

7. The dental cream composition claimed in claim 1 wherein said calcium salt is in amount to provide about 0.01 to 0.02% calcium ion in water.

8. The dental cream composition claimed in claim 1 wherein said calcium salt is calcium metasilicate.

9. The dental cream composition claimed in claim 1 wherein a magnesium salt is additionally present in amount to provide at least about 0.01 to 0.3% of magnesium ions in water.

10. The dental cream composition claimed in claim 2 wherein about 0.5 to 5% by weight of a hard abrasive selected from the group consisting of calcined alumina and zirconium silicate is additionally present.

11. The dental cream composition claimed in claim 10 wherein said hard abrasive is calcined alumina.

12. The dental cream composition claimed in claim 1 wherein about 0.25 to 10% by weight of alpha-alumina trihydrate is additionally present.

* * * * *